United States Patent
Valcore

(10) Patent No.: US 8,508,239 B2
(45) Date of Patent: Aug. 13, 2013

(54) NON-DESTRUCTIVE SIGNAL PROPAGATION SYSTEM AND METHOD TO DETERMINE SUBSTRATE INTEGRITY

(75) Inventor: John Valcore, San Jose, CA (US)

(73) Assignee: Lam Research Corporation, Fremont, CA (US)

( * ) Notice: Subject to any disclaimer, the term of this patent is extended or adjusted under 35 U.S.C. 154(b) by 393 days.

(21) Appl. No.: 12/435,934

(22) Filed: May 5, 2009

(65) Prior Publication Data

US 2010/0283482 A1    Nov. 11, 2010

(51) Int. Cl.
     *G01R 23/20*      (2006.01)

(52) U.S. Cl.
     USPC ............................................. 324/620; 73/587

(58) Field of Classification Search
     USPC .......................................................... 324/620
     See application file for complete search history.

(56) References Cited

U.S. PATENT DOCUMENTS

| | | | | |
|---|---|---|---|---|
| 3,940,952 | A * | 3/1976 | Mitchell | 73/629 |
| 5,038,615 | A * | 8/1991 | Trulson et al. | 73/597 |
| 5,113,697 | A | 5/1992 | Schlawne | |
| 5,469,742 | A * | 11/1995 | Lee et al. | 73/597 |
| 5,996,415 | A * | 12/1999 | Stanke et al. | 73/597 |
| 6,112,595 | A * | 9/2000 | Stanke et al. | 73/597 |
| 6,182,510 | B1 * | 2/2001 | Stanke et al. | 73/597 |
| 6,275,742 | B1 | 8/2001 | Sagues et al. | |
| 6,362,487 | B1 | 3/2002 | Ehlert et al. | |
| 6,413,789 | B2 * | 7/2002 | Ostapenko | 438/14 |
| 6,825,487 | B2 | 11/2004 | Preece | |
| 6,938,488 | B2 * | 9/2005 | Diaz et al. | 73/597 |
| 6,959,602 | B2 * | 11/2005 | Peterson et al. | 73/602 |
| 7,836,769 | B2 * | 11/2010 | Korbler | 73/645 |
| 7,917,317 | B2 * | 3/2011 | McKeon | 702/66 |
| 2003/0233879 | A1 | 12/2003 | Graff et al. | |
| 2007/0266789 | A1 * | 11/2007 | Hampton et al. | 73/596 |

FOREIGN PATENT DOCUMENTS

| | | |
|---|---|---|
| JP | 1141349 A | 6/1989 |
| KR | 1020070014261 A | 2/2007 |

OTHER PUBLICATIONS

Dallas, W, et al., "Resonance ultrasonic vibrations for crack detection in photovoltaic silicon wafers", *Institute of Physics Publishing, Measurement Science and Technology, Meas. Sci. Technol.* 18 (2007), Online at stacks.iop.org/MST/18/852, (Feb. 5, 2007), pp. 852-858.

Jain, et al., "Experiments in Ultrasonic Flaw Detection using a MEMS Transducer", *Carnegie Mellon University*, (2002), 9 pgs.

(Continued)

*Primary Examiner* — Arleen M Vazquez
*Assistant Examiner* — Alesa Allgood
(74) *Attorney, Agent, or Firm* — Schwegman Lundberg & Woessner, P.A.

(57) ABSTRACT

In various exemplary embodiments described herein, a system and associated method relate to non-destructive signal propagation to detect one or more defects in a substrate. The system can be built into a semiconductor process tool such as a substrate handling mechanism. The system comprises a transducer configured to convert one or more frequencies from an electrical signal into at least one mechanical pulse. The mechanical pulse is coupled to the substrate through the substrate handling mechanism. A plurality of sensors is positioned distal to the transducer and configured to be coupled, acoustically or mechanically, to the substrate. The plurality of distal sensors is further configured to detect both the mechanical pulse and any distortions to the pulse. A signal analyzer is coupled to the plurality of distal sensors to compare the detected pulse and any distortions to the pulse with a baseline response.

18 Claims, 6 Drawing Sheets

(56) References Cited

OTHER PUBLICATIONS

Ozevin, et al., "Development of MEMS Device for Acoustic Emission Testing", *Carnegie Mellon University*, (Oct. 11, 2005), 11 pgs.

"International Application Serial No. PCT/IB2010/051855, International Preliminary Report on Patentability mailed Nov. 17, 2011", 5 pgs.

* cited by examiner

US 8,508,239 B2

NON-DESTRUCTIVE SIGNAL PROPAGATION SYSTEM AND METHOD TO DETERMINE SUBSTRATE INTEGRITY

TECHNICAL FIELD

The present application relates generally to the field of semiconductor processing and, in a specific exemplary embodiment, to a system and method of determining substrate integrity by non-destructive testing.

BACKGROUND

Silicon (Si) or silicon-based substrates are frequently employed for manufacturing integrated circuits (ICs). A monocrystalline silicon substrate has a uniform lattice structure. As used in IC manufacturing, the Si substrate is typically in the form of a thin circular wafer, cut from an ingot, and varying from 100 mm to 300 mm in diameter (although both smaller and larger diameters, as well as other geometries are also used). Additionally, elemental semiconductor types other than silicon are frequently used in manufacturing ICs as well. These other elemental semiconductors, such as germanium, are materials contained in Group IV of the periodic chart. Further, compound semiconductors (e.g., compounds of elements, especially elements from periodic table Groups III-V and II-VI) have seen increased IC manufacturing activity in recent years. Compound semiconductors are frequently used for manufacturing ICs used in, for example, high-speed signal processing applications. Semiconducting alloys (e.g., $Al_xGa_{1-x}As$, $HG_{1-x}CD_xTe$) are also becoming more common in ICs. Additionally, non-semiconducting materials such as, for example, a polyethylene-terephthalate (PET) substrate deposited with silicon dioxide or a quartz photomask, each of which may be deposited with polysilicon followed by an excimer laser annealing (ELA) anneal step may also be used in certain applications for ICs and related electrical structures.

However, regardless of the substrate employed in manufacturing ICs, integrity of the substrate structure is essential in order to maximize the yield for the ICs manufactured on the substrate. Current techniques to determine structural defects within substrates include Scanning of Infrared Depolarization (SIRD) and a combination of photoluminescence and photo-thermal heterodyne spectroscopy combined with SIRD. While these techniques are able to characterize explicit crystal defects including dislocations, cracks, scratches, and foreign particulates, each of these techniques involve complex and costly test equipment that require the substrate to be analyzed offline. Offline analysis either significantly delays the overall process time of the substrate or provides results of the substrate integrity only after the substrate has been fully processed. Regardless, offline analysis is time-consuming and costly in any manufacturing or fabrication process line.

BRIEF DESCRIPTION OF DRAWINGS

Various ones of the appended drawings merely illustrate exemplary embodiments of the present invention and cannot be considered as limiting its scope.

DETAILED DESCRIPTION

Figure 1:
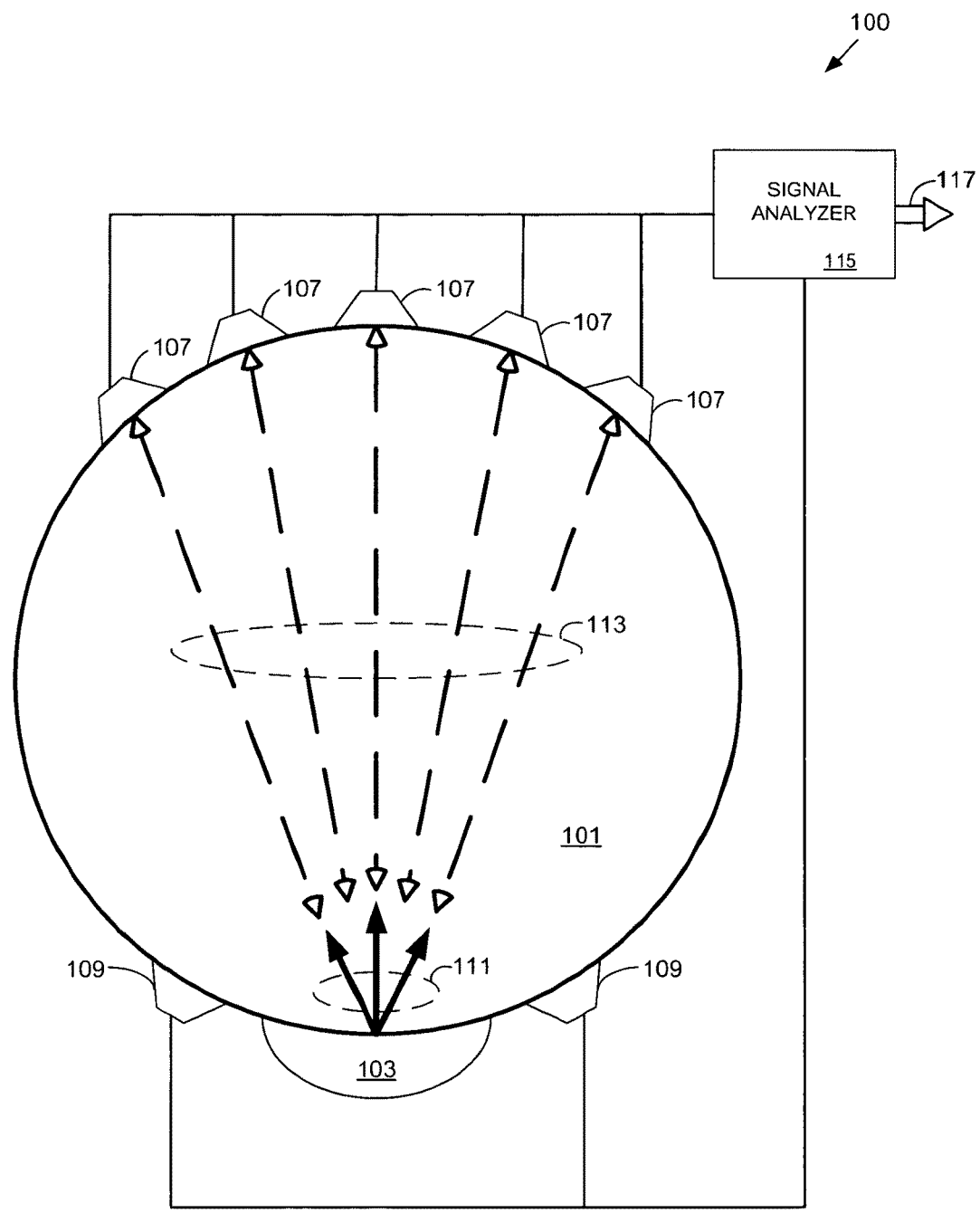
FIG. 1 is a schematic representation of an exemplary non-destructive signal propagation system to detect defects in a substrate.

The description that follows includes illustrative systems, methods, and techniques that embody the inventive subject matter. In the following description, for purposes of explanation, numerous specific details are set forth to provide an understanding of various embodiments of the inventive subject matter. It will be evident, however, to those skilled in the art that embodiments of the inventive subject matter may be practiced without these specific details. Further, well-known operations, structures, and techniques have not been shown in detail.

As used herein, the term "or" may be construed in either an inclusive or exclusive sense. Similarly, the term "exemplary" is construed merely to mean an example of something or an exemplar and not necessarily a preferred or ideal means of accomplishing a goal. Additionally, although various exemplary embodiments discussed below focus on semiconductor testing methodologies, the embodiments are given merely for clarity in disclosure. Thus, any type of non-destructive testing on a variety of, for example, non-semiconductor substrates and components, can employ various embodiments of the system and method described herein and are considered as being within a scope of the present inventive subject matter.

Moreover, various exemplary embodiments discussed herein define systems and methods to detect irregularities or other defects in, for example, semiconductor substrates. In an exemplary embodiment, a non-destructive signal propagation system to detect one or more defects in a substrate is disclosed. The system can be built into a semiconductor process tool such as a substrate handling mechanism (e.g., a robotic arm, pick-up tool, or a substrate alignment mechanism). The system comprises a transducer configured to convert one or more frequencies from an electrical signal into at least one mechanical pulse. The frequencies can be in a range of the audio spectrum. Alternatively, the frequencies can be supersonic or sub-sonic based upon factor such as a geometry and material or materials comprising the substrate. The mechanical pulse is coupled to the substrate through the substrate handling mechanism. A plurality of sensors is positioned distal to the transducer and configured to be coupled, acoustically or mechanically, to the substrate. The plurality of distal sensors is further configured to detect both the mechanical pulse and any distortions to the pulse. As noted in other exemplary embodiments, additional sensors can also be employed. Distortions to the pulse, as discussed herein, are typically created by the defects in the substrate. A signal analyzer is coupled to the plurality of distal sensors to compare the detected pulse and any distortions to the pulse with a baseline response of, for example, either a known-good substrate or a computational model of the substrate. Computational modeling of signals traversing a substrate is known independently in the art and will not be discussed in detail herein.

In another exemplary embodiment, a non-destructive signal propagation method to detect one or more defects in a substrate is disclosed. The method comprises converting one or more frequencies, in a transducer, from an electrical signal into at least one mechanical pulse, positioning the transducer to couple the at least one mechanical pulse to the substrate, and positioning a plurality of sensors distal to the transducer. The plurality of distal sensors is configured to be coupled to the substrate. The method further includes detecting the mechanical pulse and any distortions to the pulse with the plurality of distal sensors. The detected pulse and any distortions to the pulse are compared with a baseline response to detect the one or more defects. Each of these exemplary embodiments, and others, is discussed in detail, below.

Design constraints of the prior art, mentioned above, can be partially or fully obviated by providing a mechanical or acoustical signal transmitter/receiver apparatus that can exist within a semiconductor equipment transfer module. The equipment transfer module can include, for example, a wafer alignment device or a robotic handler, each known independently in the art. The wafer alignment device rotates the wafer, or other substrate, to a notch or flat on the wafer prior to insertion into the semiconductor equipment. Wafer alignment devices are commonly used within the semiconductor industry on various pieces of semiconductor equipment such as metrology tools (both in-situ and ex-situ) and process tools. Although specific details of the type of substrate defects or irregularities are not thoroughly disclosed herein, such defects are known independently to a skilled artisan. Utilizing various embodiments of the systems and methods disclosed herein, the presence of a defect is identified in-situ, thus providing significant time and cost savings for IC manufacturers.

With reference to FIG. 1, an exemplary embodiment of a non-destructive signal propagation system 100, in use, includes a substrate 101, a transducer 103, a plurality of distal sensors 107, and a plurality of proximate sensors 109. The non-destructive signal propagation system 100 further includes a signal analyzer 115. As described herein, the non-destructive signal propagation system 100 can be adapted to function with a variety of substrates used in the semiconductor and allied industries. Thus, in a specific exemplary embodiment, the substrate 101 is a silicon wafer.

The non-destructive signal propagation system 100, as described in more detail below, determines integrity of the substrate 101 by employing, for example, acoustical or mechanical signals emanating from the transducer 103. The transducer 103 imparts a mechanical vibration to the substrate 101. A signal output 111 is produced by the transducer 103. A plurality of propagated signals 113 are transmitted along the lattice structure of the substrate 101. In an exemplary embodiment, the propagated signals are received by one or more of the plurality of distal 107 and proximate 109 sensors and compared in the signal analyzer 115 with a baseline signal in one or more ways, discussed below. Any distortions to the plurality of propagated signals 113 caused by defects in the substrate 101 are also received by the plurality of distal 107 and proximate 109 sensors. The distortions are also discussed in detail, below.

The transducer 103 can be any of various device types, known independently in the art, and convert an electrical input into a sonic or ultrasonic output. For example, an electrical input, at one or more frequencies, can be provided to the transducer 103 from a signal generator (not shown but also known independently in the art). The signal generator can provide either a single pulse, a plurality of pulses with a pre-determined time between each pulse, or a continuous pulse train of one or more frequencies. A resulting output from the transducer 103 imparts the pulse or the one or more frequencies as mechanical vibrations within the substrate 101 producing the signal output 111. In a specific exemplary embodiment, the transducer 103 is an ultrasonic transmitter that applies a series of uniform pulses to the backside of the substrate 101. Further, based upon the disclosure given herein, a skilled artisan will recognize that other frequency output ranges can be employed. In certain material types and substrate geometries, a higher or lower frequency range may be appropriate.

The transducer 103 is placed in contact with the substrate 101 either on a face of the substrate 101 or on its edge. If the transducer 103 is built-in to an edge aligner or a robotic pick-up tool, the transducer 103 then makes contact with a back face of the substrate 101, typically near one edge. Contact with the back face has an advantage in reducing particulate contamination or micro-scratches on the front face of the substrate 101 as well. Various embodiments of the non-destructive signal propagation system 100 can be placed within transfer chambers or air locks of a plasma etch tool, such as a LAM 2300® Exelan® Flex™ Etch System process tool (manufactured by Lam Research® Corporation, Fremont, Calif., USA). Embodiments of the non-destructive signal propagation system 100 can also be placed directly on robotic handlers, transport mechanisms, a substrate alignment mechanism, or other substrate handling components associated with a metrology or process tool.

The plurality of distal sensors 107 and the plurality of proximate sensors 109 form at least two arrays of receivers. The plurality of proximate sensors 109 generally receives a fairly unaltered version of the signal output 111 from the transducer 103. Thus, in an exemplary embodiment, an output from the plurality of proximate sensors 109 can serve as baseline signal comparison with an output of the plurality of distal sensors 107. For example, an output signal of one or more of the plurality of distal sensors 107 is compared with an output of one or more of the plurality of proximate sensors 109 noting frequency shifts, amplitude changes, phase shifts, and so on. Alternatively or in addition, the propagated signal detected by the sensors can be compared to a baseline signature of a known-good substrate. In another alternative embodiment, the propagated signal can be compared with a moving average signal where the moving average is based upon a prior group of substrates. Various combinations of these comparison techniques can readily be employed as needed for a given operation or process.

In a specific exemplary embodiment, each of the plurality of distal sensors 107 and the plurality of proximate sensors 109 is comprised of micro-electromechanical systems (MEMS, known independently in the art) that act as receivers of the signal transmitted by the transducer 103. The plurality of distal sensors 107 and the plurality of proximate sensors 109 relay the frequency, amplitude, and phase correlating to both the signal output 111 and the plurality of propagated signals 113 detected.

The signal analyzer 115 is coupled to each of the plurality of distal sensors 107 and the plurality of proximate sensors 109 and provides an output 117 of the analyzed signal. The analyzed signal can be displayed on, for example, a digital oscilloscope. In a specific exemplary embodiment (not shown but recognizable to a skilled artisan after reading the disclosure provided herein), the output 117 can provide the analyzed signal to an automated system that compares a signal from a wafer under test to an expected signal response from a baseline, known-good substrate, or moving average of substrates as discussed briefly above. Such an automated system can be based on one or more of a hardware, firmware, or software structure. The signal comparison from the substrate under test to the baseline can function as a go/no-go gauge to provide a rapid determination of the suitability of any substrate in a process environment.

In another exemplary embodiment, the substrate 101 is characterized both pre- and post-process with a negligible effect to product throughput due to the brief time required for substrate analysis with the system. For a substrate of full integrity with a uniform periodic crystalline structure, the plurality of propagated signals 113 is uniformly distributed across a given array of receivers (i.e., either one or more of the plurality of distal sensors 107 or the plurality of proximate sensors 109) per a given set of boundary conditions based upon specific structural dimensions of the substrate.

A substrate possessing a uniform and homogeneous structure has a characteristic impedance that spans the entire lattice structure. The characteristic impedance provides a repeatable means of assessing the structural integrity of the substrate by monitoring the plurality of propagated signals 113 as the signals traverse the substrate. For example, when a Gaussian acoustical pulse is applied to the substrate 101 at a given node, the pulse travels along the medium as a function of its impedance. The impedance is comprised of the density of the substrate, the distance between molecules within the substrate, and the velocity of the speed of sound within the substrate (assuming a signal applied that is within the audio portion of the spectrum).

Figure 2:
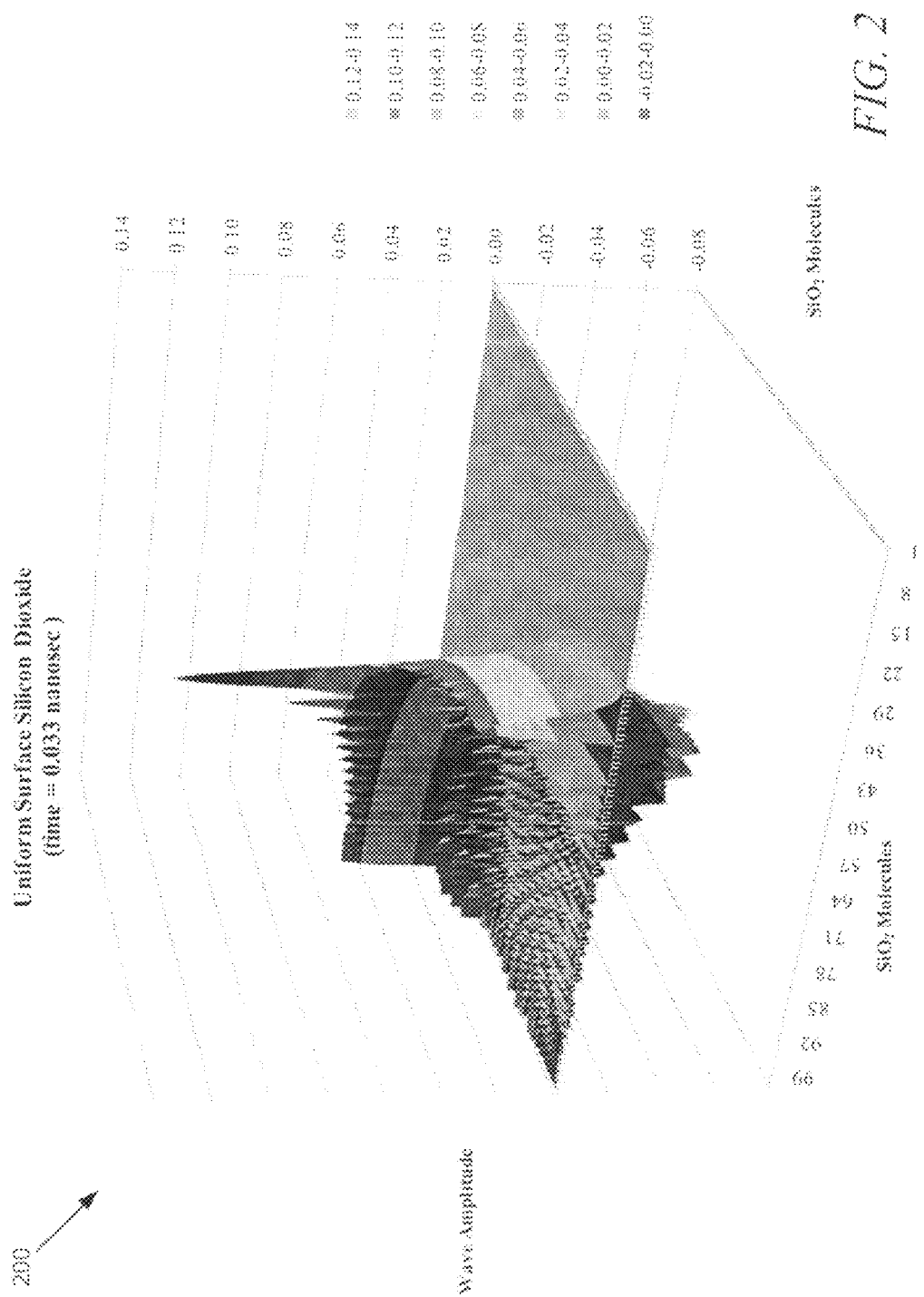
FIG. 2 is an exemplary graphical representation of a signal response for a substantially uniform substrate, the exemplary graphical response can either be employed within or produced by the system of FIG. 1.

Referring now to a FIG. 2, a uniform-substrate signal propagation graph 200 illustrates an acoustical pulse traveling across a uniform silicon dioxide ($SiO_2$) plane of a substrate. The uniform-substrate signal propagation graph 200 was simulated in MATLAB® as a 100 by 100 matrix of $SiO_2$ molecules (boundary conditions were ignored for the simulation). Notice the attenuation of the signal as it propagates along the $SiO_2$ plane as well as the dispersion of the wave across the entire breadth of the surface. When the interference of the edges of the substrate is accounted for, an entire map can be created of a surface of the substrate. The map can then be used as a baseline for comparison with a measured substrate response in detecting surface or sub-surface abnormalities that could be incurred after the substrate is processed or handled. (While not shown directly, a similar map can be produced to examine bulk defects within the substrate as well.)

With reference again to FIG. 1, an occurrence of defects within the substrate 101 alters the signal path, thereby altering the plurality of propagated signals 113. The occurrence of defects can cause an impedance mismatch on or in the substrate 101 with regard to the plurality of propagated signals 113 causing one or more of the signals to head back toward the transducer 103. Consequently, non-uniformities occur in a distribution of signals seen by the plurality of distal 107 and proximate 109 sensors. An analysis of the received signal distribution thus provides details as to the relative location of the defect with respect to the plurality of sensors as well as the magnitude of the defect. The relative location is determined upon a known spatial distribution of the plurality of distal 107 and proximate 109 sensors.

When the integrity of the substrate surface is altered or non-uniform, as a result of a microscopic crack or lattice dislocations, the distance between nodes within at least a portion of the lattice structure is altered. The altered distance shifts both the amplitude and the phase of the signal. Consequently, the signal deviates from the signal response measured on a uniform (i.e., homogeneous) surface. The signal in the non-uniform substrate is also reflected back towards the transducer 103, while the forward propagating signal has an attenuated amplitude (see the plurality of propagated signals 113 at FIG. 1).

Figure 3:
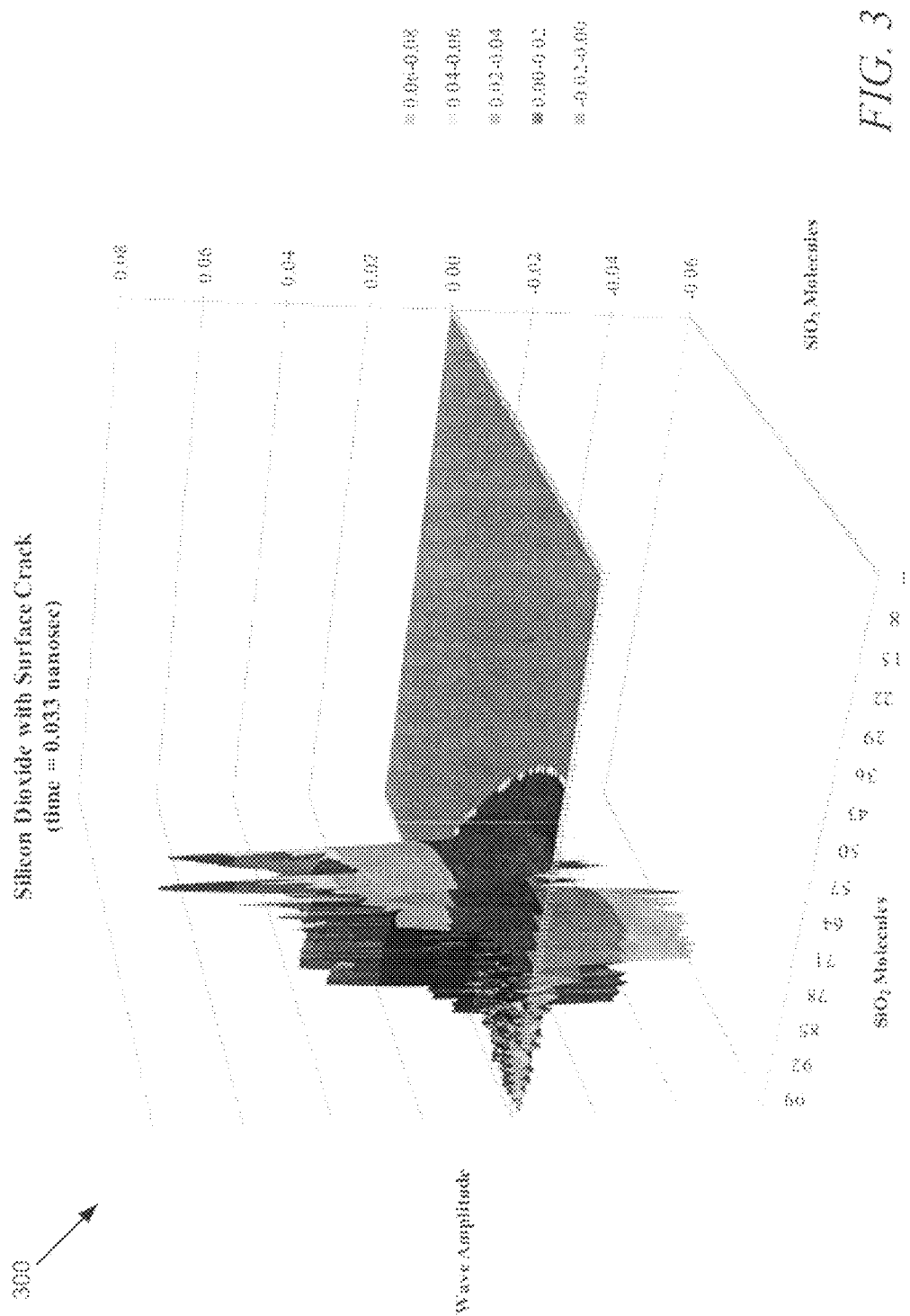
FIG. 3 is an exemplary graphical representation of a signal response for a substrate having a surface, the exemplary graphical response can either be employed within or produced by the system of FIG. 1.

With reference now to FIG. 3, a non-uniform-substrate signal propagation graph 300 illustrates an acoustical pulse traveling across a non-uniform $SiO_2$ plane of a substrate. When the integrity of a surface of the substrate, here an $SiO_2$ film overlaying the substrate, the surface of the substrate is altered and can produce a microscopic crack. Thus, the distance between nodes within the lattice structure is varied. The variation in the lattice structure causes both the amplitude and phase of an applied signal to shift, deviating from the response of the signal when measured on a uniform surface (see FIG. 2). The signal will also be reflected back towards the source, while the forward propagating wave will have an attenuated amplitude.

The non-uniform $SiO_2$ plane was simulated in MATLAB® by increasing the distance of five $SiO_2$ molecules in the 100× 100 matrix molecule array used in the FIG. 2 simulation. By monitoring both the amplitude and phase of the emitted signal at opposing ends of the substrate surface through the array of sensors, variations across the entire surface area of the substrate can be quantified and qualified.

Thus, in a specific exemplary embodiment, the inventive subject matter described herein serves to verify the integrity of a substrate used for the manufacturing of ICs. A mechanical or acoustical transducer is placed in contact with the backside of the substrate. A pulse is generated that propagates through the crystalline structure of the substrate and an array of sensors collects the signal response. A midpoint of the array can be physically placed, for example, 180 degrees from the point of transmission (i.e., the transducer) of the pulse. The distribution of the signal response enables the system to determine if the lattice structure of the substrate is maintained given that microscopic and macroscopic cracks within the substrate structure will alter the signal path and cause non-uniform distributions of the signal propagated through the altered signal path. Therefor, the system can measure the integrity of the substrate, both pre- and post-process, and defects can be detected before the substrate, such as a silicon wafer, is needlessly processed.

For example, in a typical IC fabrication process, a silicon wafer undergoes a number of plasma-based processes. The wafer is subjected to stresses within each plasma process induced by both non-uniform clamp force caused by an electrostatic chuck (ESC), used to secure the wafer to the process tool, as well as temperature non-uniformities on the wafer surface due to wafer placement within the chamber, subsequent plasma non-uniformities that ensue, and stresses induced by films applied to the wafer. The stresses can produce hairline cracks on the wafer, thereby degrading the integrity of the wafer and causing it to be highly susceptible to full fracturing during mechanical handling after processing. Given the number of plasma-based process steps alone that occur on multiple tools in order to fully manufacture ICs on a given substrate, being able to detect substrate flaws at any given stage of the manufacturing process prevents a large expenditure of both time and money associated with processing a substrate that will have an unsatisfactory yield. Consequently, by detecting such defects at the outset of a given process, considerable time, energy, and money are saved. A root-cause analysis of the defect can be conducted as spatial coordinates of the defect can be recorded and retrieved for later ex-situ analysis. A signal processing unit can provide a signal to a host computer characterizing either the surface or the bulk of the wafer. An output from the signal processing unit can denote a degree of wafer integrity, and the location of any defects based upon responses from each of the plurality of sensors.

With reference again briefly to FIG. 1, a proof-of-concept test was conducted to verify both placement and mechanical contact repeatability of the transducer 103 with reference to the substrate 101. For this specific test, a 2 kHz signal at 950 mV was fed into a modified audio transducer (manufactured by Macally USA Mace Group, Inc., Ontario, Calif.), used as the transducer 103. Two piezoelectric sensors (manufactured by Measurement Specialties, Hampton, Va., USA) were employed as the plurality of distal sensors 107. A 300 mm silicon wafer was used as the substrate 101 and was placed repeatedly onto a modified aluminum dynamic alignment fixture. The output 117 from the test setup was fed into a Tektronix TDS 5104B series oscilloscope (manufactured by Tektronix, Inc., Beaverton, Oreg., USA). The wafer notch was used as a feature of interest. The transducer 103 was repeatedly placed either 2 mm or 4 mm from the feature of interest.

Figure 4:
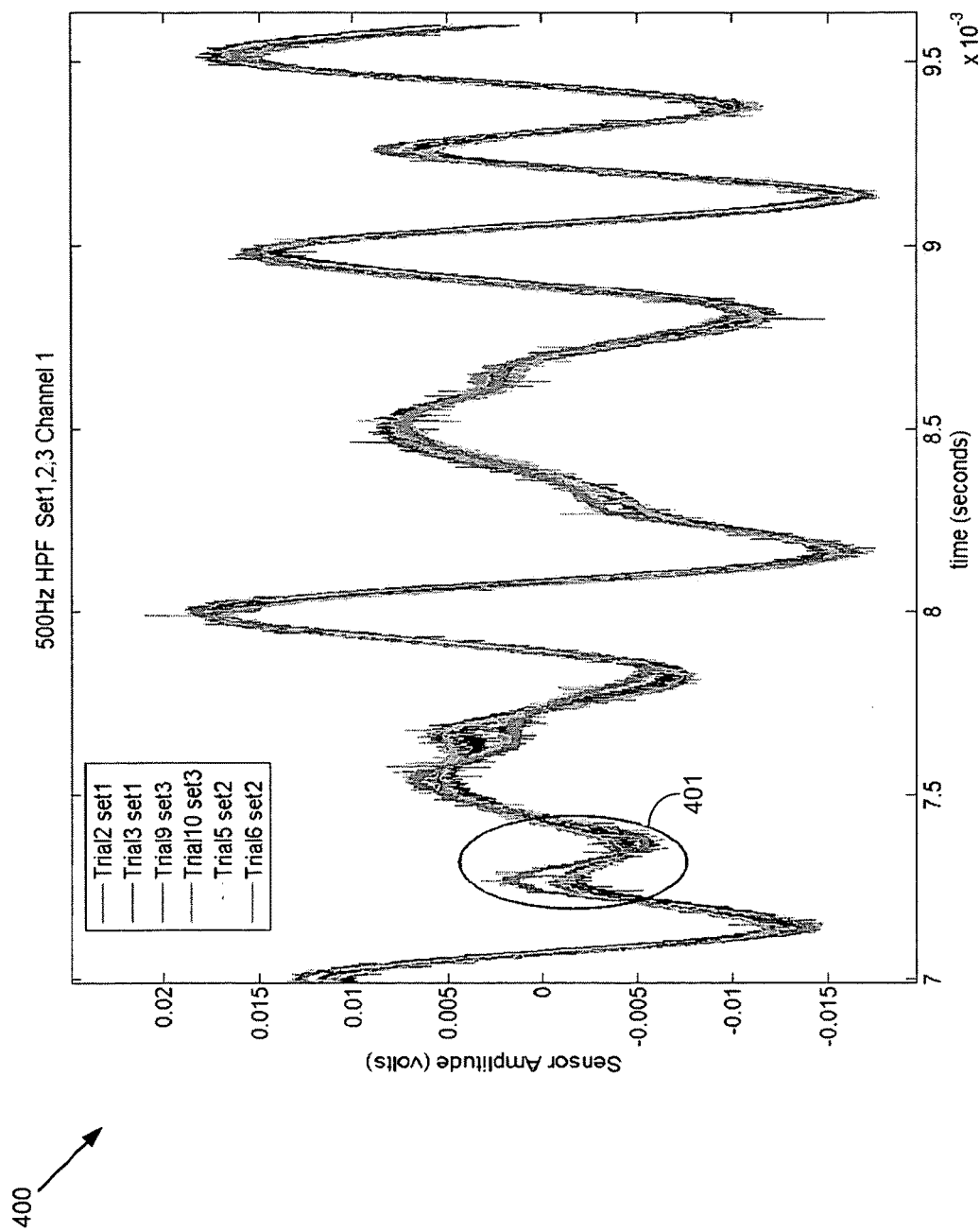
FIG. 4 is an exemplary graphical representation of a sensor-received signal response as a function of time using the system of FIG. 1.

With reference now to FIG. 4, a sensor-received signal response graph 400 indicates the frequency composition of both of the piezoelectric sensors used in the proof-of-concept test. A frequency shift location 401 is noted as the distance between the audio transducer and the feature of interest increased. The frequency shift location 401 indicates that as the distance increased, the amplitude of the first harmonic frequency (i.e., 4 kHz) increased while the amplitude of the fundamental frequency (i.e., 2 kHz) decreased.

Figure 5:
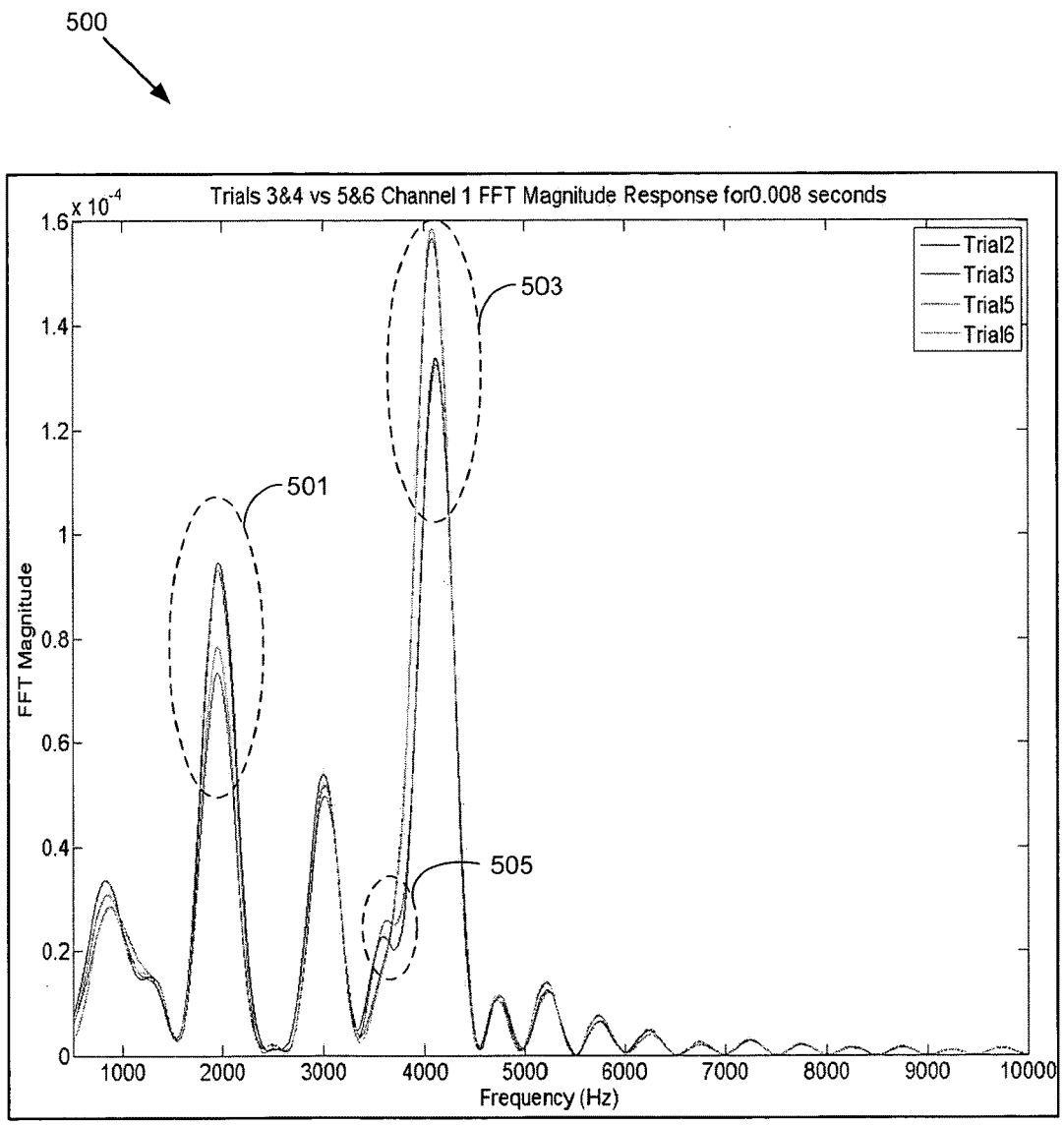
FIG. 5 is an exemplary graphical representation of a Fast Fourier Transform (FFT) response as a function of frequency using the system of FIG. 1.

Referring now to FIG. 5, a Fast Fourier Transform (FFT) signal response graph 500 indicates harmonic shifts in a frequency domain but is otherwise similar to the time-domain-based sensor-received signal response graph 400 of FIG. 4. A first fundamental frequency shift location 501 indicates an approximately 18% decrease in amplitude of the fundamental frequency (note the 2 kHz fundamental frequency indicated on the abscissa) when the audio transducer is moved from 2 mm to 4 mm away from the feature of interest. Similarly, a first harmonic shift location 503 indicates an approximately 23% increase in amplitude of the first harmonic frequency (note the 4 kHz frequency indicated on the abscissa) when the audio transducer is moved from 2 mm to 4 mm away from the feature of interest. Also, a second harmonic shift location 505 indicates a shift in a sideband to the 4 kHz first harmonic frequency. The second harmonic shift location 505 is produced only when the audio transducer is the 4 mm distance from the feature of interest.

Thus, FIGS. 4 and 5 confirm that the harmonic content of the signal response is a function of the distance from the audio transducer to the feature of interest. The testing further revealed a high degree of repeatability between non-consecutive trials with an $R^2$ correlation greater than 0.99. Given that the commutative property exists for signals such as the one utilized in the proof-of-concept testing leads directly to two additional conclusions: (1) for a fixed transducer, a broadband signal response will be a function of the location of a given feature on a surface of the substrate; and (2) the method to identify features on or in the substrate allows both identification of the existence of any surface or molecular variations on or in the substrate as well as the size and location of the surface or molecular variations.

Figure 6:
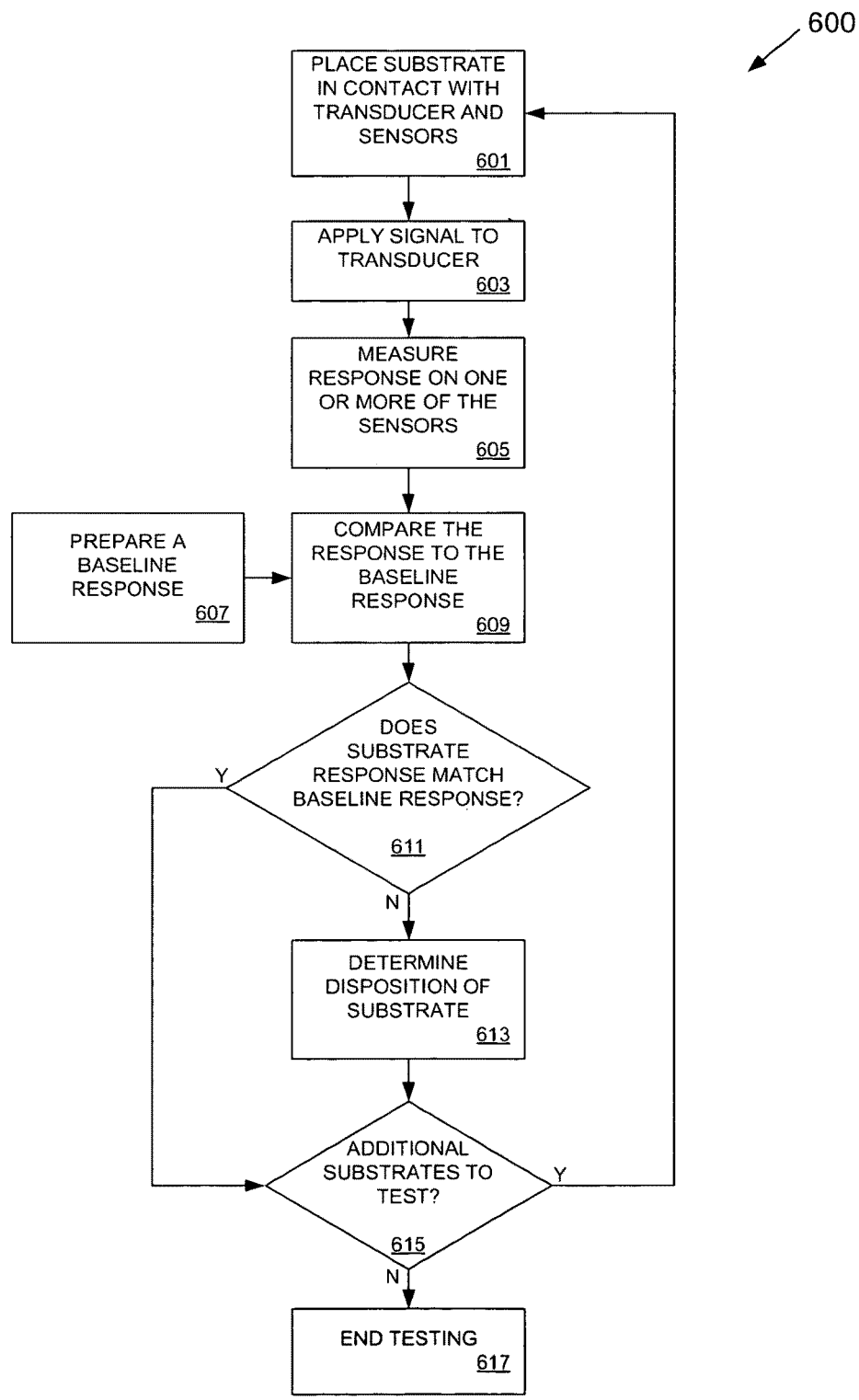
FIG. 6 is a flowchart depicting an exemplary method for detecting irregularities in a substrate.

With reference to FIG. 6, a flowchart 600 depicts an exemplary method for detecting irregularities in a substrate. An operation 601, a substrate, for example a silicon wafer, is placed in contact with the transducer and the plurality of sensors. The transducer and the plurality of sensors will typically be embedded into a portion of the process or metrology tool, as discussed above. A signal is then applied to the transducer, an operation 603, and consequently, to the substrate. As discussed herein, the signal can be a variety of either single-frequency signals, or a broadband signal in the form of, for example, a square wave. Also, depending upon an exact application and the substrate used, the frequency or frequency range can be found in an audio portion of the electromagnetic spectrum, supersonic to the audio spectrum, or any radio frequency range or higher. For certain applications, a frequency or frequency range below the audio spectrum (i.e., subsonic) can also be appropriate.

After the signal is applied to the transducer, the response on one or more of the plurality of sensors is measured at operation 605. Although not shown explicitly, the response measurement can be repeated as needed to, for example, increase a signal to noise ratio of the measurement operation. Either subsequent to or concurrent with the response measurement process, a baseline response is prepared at operation 607. The baseline response can be prepared in a number of ways. For example, as discussed herein, the baseline response can be based upon a computationally-derived model, a known-good substrate, a moving average of substrate responses, or by a variety of other means known independently to a person of skill in the art upon reading the material disclosed herein.

At operation 609, the response on one or more of the plurality of sensors is compared to the baseline response. A determination is then made at operation 611 whether the substrate measured response matches the baseline response. If the substrate measured response does not match the baseline response, a disposition of the substrate is determined at operation 613. The disposition can be based on a pre-determined magnitude of the difference between the substrate measured response and the baseline response. A result of the disposition can include can include, for example, merely removing the substrate from the process line. Alternatively, the disposition can include returning the substrate for rework in processes earlier in a fabrication line or sending the substrate for ex-situ metrology for root-cause determination of defects detected. Once a determination has been made of the disposition of the substrate at operation 613, a further determination is made whether there are any additional substrates to test at operation 615. If there are additional substrates to test, based on, for example, a known lot size, tracking identification numbers on substrates, or a known number of substrates and a substrate carrier, then the exemplary method of FIG. 6 loops back to operation 601. If a determination is made that there are no additional substrates to test, at operation 615, then the testing is ended at operation 617.

If, at operation 611, a determination is made that a substrate measured response does match the baseline response, the exemplary method continues at operation 615. A determination is then made whether there are additional substrates to test and the exemplary method continues as described above.

A skilled artisan will quickly recognize that the exemplary system and method for detecting irregularities in a substrate described herein can be employed at multiple points in a process line. For example, a measurement can be made of incoming silicon wafers in an IC fabrication line prior to a pre-oxidation cleaning step. As the wafers continue in the process flow, an additional measurement can be made prior to each subsequent deposition and etch process step. Alternatively, the wafers can be scanned immediately prior or subsequent to each stress-inducing process step, such as those involving plasma-based processes. The skilled artisan will further recognize that the system and method can be readily incorporated into a plurality of both process and metrology tools with very little impact on a total time to measure each wafer in, for example, a front-end-of-line process.

Although an overview of the inventive subject matter has been described with reference to specific exemplary embodiments, various modifications and changes may be made to these embodiments without departing from the broader spirit and scope of the present invention. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. For example, the disclosure provided herein details numerous exemplary embodiment embodiments with regard to particular semiconductor substrates. However, the disclosure can be applied to non-semiconductor based components such as, for example, detecting and characterizing defects within portions of the semiconductor process tools, such as the ESC described above. Further, some components, such as the signal analyzer of FIG. 1, can be produced from hardware, firmware, software, or various combinations thereof. The Detailed Description, therefore, is not to be taken in a limiting sense, and the scope of various embodiments is defined only by the appended claims, along with the full range of equivalents to which such claims are entitled.

Moreover, plural instances may be provided for structural elements or operations described herein as a single instance. Other allocations of functionality are envisioned and may fall within a scope of various embodiments of the present invention. In general, structures and functionality presented as separate resources in the exemplary configurations may be implemented as a combined structure or resource. Similarly, structures and functionality presented as a single resource may be implemented as separate resources.

Additionally, many industries allied with the semiconductor industry could make use of the strain-compensation technique. For example, a thin-film head (TFH) process in the data storage industry, an active matrix liquid crystal display (AMLCD) in the flat panel display industry, or the microelectromechanical (MEM) industry could readily make use of the processes and techniques described herein. The term "semiconductor" should thus be recognized as including the aforementioned and related industries. These and other variations, modifications, additions, and improvements fall within a scope of the present invention as represented by the appended claims. The specification and drawings are, accordingly, to be regarded in an illustrative rather than a restrictive sense.

What is claimed is:

1. A non-destructive signal propagation system to detect one or more defects in a substrate, the system comprising:
    a transducer to convert one or more frequencies from an electrical signal into at least one mechanical pulse, the at least one mechanical pulse to be coupled to the substrate;
    a plurality of sensors to be positioned on the substrate distal to the transducer, the plurality of distal sensors to detect the at least one mechanical pulse and any distortions to the at least one mechanical pulse received from a bulk of the substrate; and
    a signal analyzer coupled to the plurality of distal sensors to compare the detected at least one mechanical pulse and any distortions to the at least one mechanical pulse received from the bulk of the substrate with a baseline response, the baseline response being based on at least one of the following comparison tools where the comparison tools are selectable from a computational model, a known-good substrate, and a moving average of a plurality of substrates.

2. The system of claim 1, further comprising a plurality of sensors positioned proximate to the transducer and coupled to the signal analyzer, the plurality of proximate sensors to be coupled to the substrate to detect any additional distortions to the at least one mechanical pulse received from the substrate.

3. The system of claim 1, wherein the one or more frequencies is within an audio portion of the electromagnetic spectrum.

4. The system of claim 1, wherein the one or more frequencies is above an audio portion of the electromagnetic spectrum.

5. The system of claim 1, wherein the one or more frequencies is provided to the transducer as a single pulse.

6. The system of claim 1, wherein the one or more frequencies is provided to the transducer as a series of pulses.

7. The system of claim 1, wherein the system is built into a substrate handling mechanism associated with a piece of semiconductor equipment.

8. A non-destructive signal propagation method to detect one or more defects in a substrate, the method comprising:
    converting one or more frequencies, in a transducer, from an electrical signal into a series of mechanical pulses;
    positioning the transducer on the substrate to couple the series of mechanical pulses to the substrate;
    positioning a plurality of distal sensors on the substrate and distal to the transducer;
    detecting the series of mechanical pulses and any distortions to the series of mechanical pulses received from a bulk of the substrate with the plurality of distal sensors; and
    comparing the detected series of mechanical pulses and any distortions to the series of mechanical pulses received from the bulk of the substrate with a baseline response to detect the one or more defects, the comparing performed using comparison tools selectable from a computational model, a known-good substrate, and a moving average of a plurality of substrates.

9. The method of claim 8, further comprising positioning a plurality of sensors on the substrate proximate to the transducer to detect any additional distortions to the at least one mechanical pulse received from the substrate.

10. The method of claim 8, further comprising selecting the one or more frequencies to be within an audio portion of the electromagnetic spectrum.

11. The method of claim 8, further comprising selecting the one or more frequencies to be above an audio portion of the electromagnetic spectrum.

12. The method of claim 8, further comprising applying the one or more frequencies to the transducer as a single pulse.

13. The method of claim 8, further comprising determining a disposition of the substrate based on a result that the one or more defects exists in the substrate.

14. A non-destructive signal propagation system for detecting one or more defects in a substrate, the system comprising:
    a converting means for converting one or more frequencies from an electrical signal into a series of mechanical pulses that are coupled to the substrate;

a primary sensing means for coupling to the substrate and detecting the series of mechanical pulses and any distortions to the series of mechanical pulses received from a bulk of the substrate, the primary sensing means being located distal to the converting means; and an analysis means for comparing the detected series of mechanical pulses and any distortions to the series of mechanical pulses received from the bulk of the substrate with a baseline response.

15. The system of claim 14, further comprising a secondary sensing means for detecting any distortion in the series of mechanical pulses received from the substrate due to an impedance mismatch in the substrate.

16. A non-destructive signal propagation system to detect one or more defects in a substrate, the system comprising:
 a substrate handling mechanism; the substrate handling mechanism including
  a transducer to convert one or more frequencies from an electrical signal into at least one mechanical pulse, the at least one mechanical pulse to be coupled to the substrate;
  a plurality of sensors to be positioned on the substrate distal to the transducer, the plurality of distal sensors to detect the at least one mechanical pulse and any distortions to the at least one mechanical pulse received from a bulk of the substrate; and
  a plurality of sensors to be positioned on the substrate proximate to the transducer, the plurality of proximate sensors to detect the at least one mechanical pulse and to detect any additional distortions to the at least one mechanical pulse received from the bulk of the substrate; and
 a signal analyzer coupled to the plurality of distal sensors and the plurality of proximate sensors to compare the detected at least one mechanical pulse and any distortions to the at least one mechanical pulse received from the bulk of the substrate with a baseline response, the baseline response being based on at least one of the following comparison tools where the comparison tools are selectable from a computational model, a known-good substrate, and a moving average of a plurality of substrates.

17. A non-destructive signal propagation system to detect one or more defects in a silicon wafer, the system comprising:
 a transducer to convert one or more frequencies from an electrical signal into at least one mechanical pulse, the at least one mechanical pulse to be coupled to the silicon wafer to be propagated along a lattice structure within the silicon wafer;
 a plurality of sensors to be positioned on the silicon wafer distal to the transducer, the plurality of distal sensors to detect the at least one mechanical pulse and any distortions to the at least one mechanical pulse received from lattice structure of the silicon wafer; and
 a signal analyzer coupled to the plurality of distal sensors to compare the detected at least one mechanical pulse and any distortions to the at least one mechanical pulse received from the lattice structure of the silicon wafer with a baseline response, the baseline response being based on at least one of the following comparison tools where the comparison tools are selectable from a computational model, a known-good substrate, and a moving average of a plurality of substrates.

18. The system of claim 17, further comprising a plurality of sensors to be positioned on the silicon wafer proximate to the transducer and coupled to the signal analyzer to receive any additional distortions to the at least one mechanical pulse received from the silicon wafer.

* * * * *

UNITED STATES PATENT AND TRADEMARK OFFICE
CERTIFICATE OF CORRECTION

| | | |
|---|---|---|
| PATENT NO. | : 8,508,239 B2 | Page 1 of 1 |
| APPLICATION NO. | : 12/435934 | |
| DATED | : August 13, 2013 | |
| INVENTOR(S) | : John Valcore | |

It is certified that error appears in the above-identified patent and that said Letters Patent is hereby corrected as shown below:

On the Title page, in column 2, under "Other Publications", line 1, delete "W," and insert --W.,-- therefor In the Specification In column 6, line 7, after "substrate", insert --is non-uniform--, therefor In column 8, line 35, after "disposition", delete "can include", therefor Signed and Sealed this
Tenth Day of December, 2013

Margaret A. Focarino
*Commissioner for Patents of the United States Patent and Trademark Office*